United States Patent
Nisch et al.

(10) Patent No.: US 6,315,940 B1
(45) Date of Patent: Nov. 13, 2001

(54) MICROELEMENT DEVICE

(75) Inventors: Wilfried Nisch, Tübingen; Alfred Stett, Reutlingen; Ulrich Egert, Reutlingen; Martin Stelzle, Reutlingen, all of (DE)

(73) Assignee: NMI Naturwissenschaftliches und Medizinisches Institut an der Universitat Tubingen in Reutlingen (DE)

( * ) Notice: Subject to any disclaimer, the term of this patent is extended or adjusted under 35 U.S.C. 154(b) by 0 days.

(21) Appl. No.: 09/311,780

(22) Filed: May 13, 1999

Related U.S. Application Data

(63) Continuation of application No. PCT/EP97/06285, filed on Nov. 11, 1997.

(30) Foreign Application Priority Data

Nov. 16, 1996 (DE) ............................................. 196 47 525
Mar. 24, 1997 (DE) ............................................. 197 12 309

(51) Int. Cl.⁷ ........................... G01N 27/26; C12M 1/34; C12M 1/42
(52) U.S. Cl. ........................ 264/600; 204/403; 204/450; 435/285.2; 435/287.1; 435/287.3; 435/288.3; 435/288.4; 422/101
(58) Field of Search .............................. 435/283.1, 285.2, 435/287.1, 287.3, 288.3, 288.4, 173.1, 173.2, 173.3, 173.4, 173.5, 173.6, 173.7, 173.8, 173.9; 422/98, 101; 204/403, 600, 450, 409, 400; 436/63, 177, 149, 150, 151

(56) References Cited

U.S. PATENT DOCUMENTS

| | | | |
|---|---|---|---|
| 4,729,949 | * 3/1988 | Weinreb et al. | 435/30 |
| 4,894,343 | * 1/1990 | Tanaka et al. | 435/301 |
| 4,895,805 | * 1/1990 | Sato et al. | 435/286 |
| 5,154,814 | * 10/1992 | Kawamura et al. | 435/287 X |
| 5,173,158 | 12/1992 | Schmukler | 435/450 |
| 5,183,744 | * 2/1993 | Kawamura et al. | 435/30 |
| 5,283,194 | * 2/1994 | Schmukler et al. | 435/287 |
| 5,308,757 | * 5/1994 | Kawamura et al. | 435/29 |
| 5,310,674 | * 5/1994 | Weinreb et al. | 435/293 |
| 5,506,141 | * 4/1996 | Weinreb et al. | 435/309.1 |
| 5,532,128 | * 7/1996 | Eggers et al. | 435/16 |
| 5,632,957 | * 5/1997 | Heller et al. | 422/68.1 |
| 5,730,850 | * 3/1998 | Kambara et al. | 204/603 |
| 5,837,198 | * 11/1998 | Itani | 422/63 |
| 5,843,767 | * 12/1998 | Beattie | 435/287.1 |
| 5,846,708 | * 12/1998 | Hollis et al. | 435/6 |
| 5,849,486 | * 12/1998 | Heller et al. | 435/6 |
| 5,981,268 | * 11/1999 | Kovacs et al. | 435/287.1 |
| 6,033,916 | * 3/2000 | Sieben et al. | 436/518 |
| 6,099,803 | * 8/2000 | Ackley et al. | 422/68.1 |
| 6,225,059 | * 5/2001 | Ackley et al. | 435/6 |
| 6,238,624 | * 5/2001 | Heller et al. | 422/68.1 |

FOREIGN PATENT DOCUMENTS

| | | |
|---|---|---|
| 19512117 A1 | 4/1995 | (DE) . |
| 19646505 A1 | 11/1996 | (DE) . |
| 0 094 193 | 5/1983 | (EP) . |
| 0 689 051 A2 | 6/1995 | (EP) . |
| WO 85/02201 | 11/1984 | (WO) . |
| WO 85/92201 | 5/1985 | (WO) . |
| WO 96/04547 | * 2/1996 | (WO) . |
| WO 96/32467 | 4/1996 | (WO) . |

\* cited by examiner

*Primary Examiner*—Jill Warden
*Assistant Examiner*—John S. Starsiak, Jr.
(74) *Attorney, Agent, or Firm*—Oppenheimer Wolff & Donnelly LLP; Claude A. S. Hamrick

(57) ABSTRACT

A microelement device has a plurality of microelements, which may be configured as microelectrodes, arranged on a substrate and adapted for making contact to cells present in a liquid environment. The cells are guided onto the microelectrodes, are isolated or are mechanically attracted to the microelectrodes. A negative-pressure force or a hydrodynamic force may be applied on the cells. Also described are a method for making contact to the cells, and a method for manufacturing the microelement device is disclosed.

38 Claims, 3 Drawing Sheets

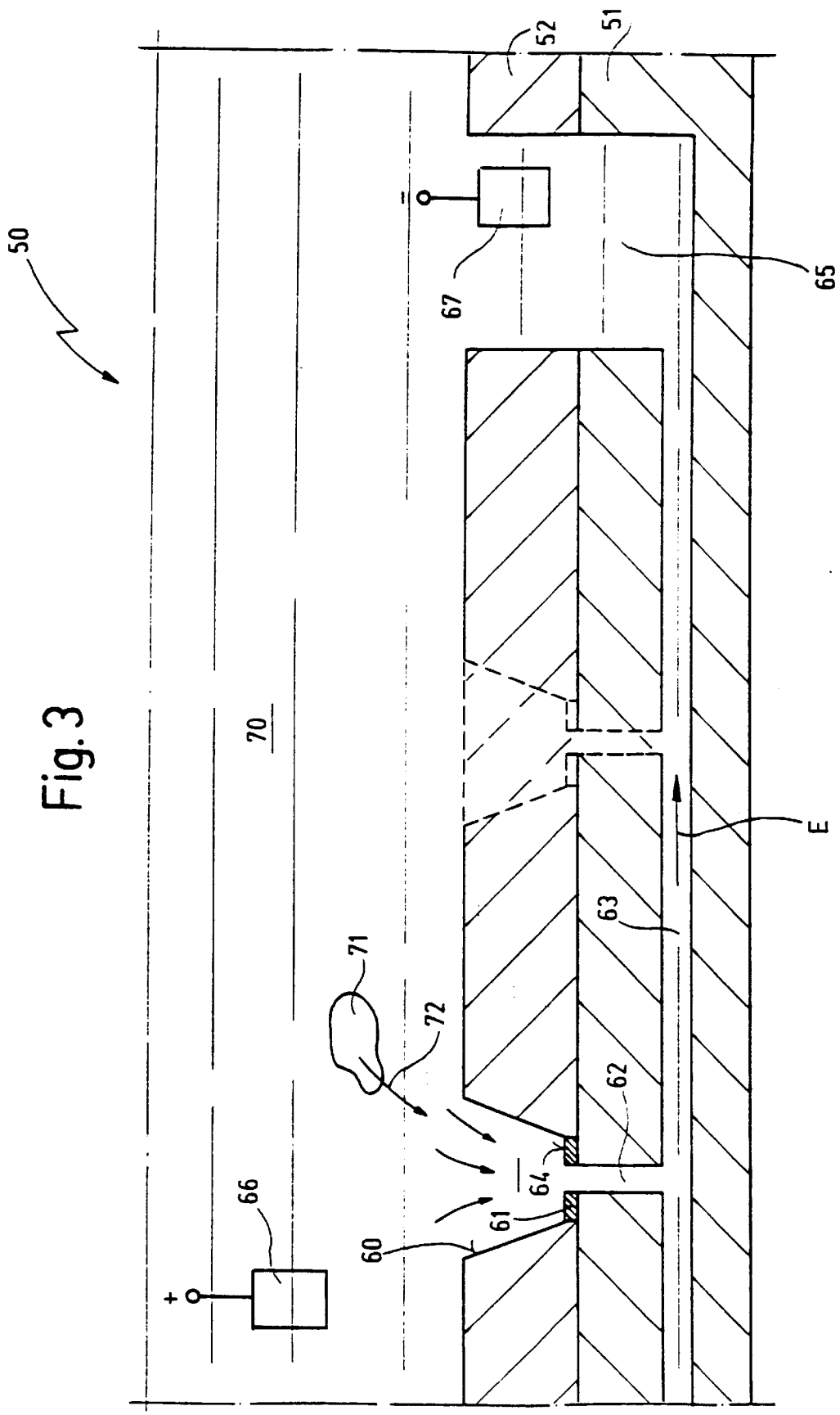

MICROELEMENT DEVICE

RELATED APPLICATIONS

The application is a continuation application of international patent application PCT/EP97/06285 filed on Nov. 11, 1997 which claims priority of German patent applications 196 47 525.2 filed on Nov. 16, 1996 and 197 12 309.0 filed on Mar. 24, 1997.

BACKGROUND OF THE INVENTION

The present invention relates to a microelement device having a plurality of microelements, arranged on a substrate, for making contact to cells present in a liquid, preferably biological environment.

The invention further relates to a method for making contact to cells present in a liquid, preferably biological, environment above a substrate, in which a contact is created between the cells and microelements.

Lastly, the invention relates to a method for manufacturing a microelement device having a plurality of microelectrodes, in which the microelements are arranged on a substrate.

It is known to use so-called microelectrode devices for the investigation of biological cells. The microelectrode electrodes serve in this context, for example, to stimulate the cells or to sense potentials. The investigations can be conducted in a biological environment or in an artificial environment. This can be, for example, a suspension having artificial vesicles made of lipids, pores being incorporated into the vesicle shell as a model system for biological cells. For this purpose the arrangements comprise, on a substrate, a plurality of microelectrodes whose dimensions are of approximately the order of magnitude of the cells, i.e. in the range from a few $\mu$m to several tens of $\mu$m.

German Patent Application P 195 29 371, of earlier priority but not previously published, discloses a microelectrode device of this kind.

To measure bioluminescence or chemoluminescence, e.g. as a reaction to chemical stimulus (toxins, drugs), and to measure changes in light absorption caused by such a stimulus when a light source is used above the cells, it is possible to utilize light-sensitive microelements, for example microphotodiodes, which are sensitive to specific spectral regions.

Microelectrodes, microphotodiodes, and the like are referred to globally, in the context of the present invention, as "microelements."

The following problems, inter alia, arise with microelectrode arrangements of conventional type and with the methods carried out therewith:

When the microelement device is brought into contact with a suspension, i.e. a liquid, for example biological, environment in which cells are present, it is more or less a matter of chance whether one cell or another settles on a specific electrode. In practice, the cells can generally be caused to settle on an electrode only with partial coverage, so that stimulation of the cell or sensing of a cell potential is confined to that partial surface. When the cell is stimulated, for example, a portion of the stimulation energy is lost in the suspension which acts as the electrolyte.

In addition, the cells only rest loosely on the electrodes. This can result in problems in terms of sealing resistance with respect to the reference electrode. In addition, the contact is very sensitive and is disrupted in response to even extremely small mechanical influences, since the cells detach from the contact.

SUMMARY OF THE INVENTION

It is therefore the object of the invention to provide an improved microelement device which eliminates the problems cited above. It is a second object of the invention to disclose a method of making such a microelement device. It is a further object of the invention to provide a method for making contact to biological cells. The intention in particular is to make it possible to bring individual cells in controlled fashion from a liquid environment into contact with the microelements and to make good contact there.

These and other objects are achieved by a microelement device which comprises means for guiding and/or isolating and/or mechanically attracting the cells onto the microelements.

With respect to the method for making contact to cells, this object is achieved, according to the present invention, by the fact that a guiding force and/or attractive force is generated between the cells and the microelements or the substrate.

Lastly, in the case of the method of making such a microelement device, the object is achieved, according to the present invention, by the fact that the substrate is manufactured at least from a base plate and a cover plate located thereabove.

Two advantages result from the fact that the cells are mechanically attracted to the microelements:

As long as the cells are still located unconstrainedly in the liquid environment, the result of the attractive force is that the cells move in controlled fashion onto the elements. It is therefore no longer a matter of chance whether one or the other cell settles on a predefined microelement.

As has already been mentioned, the present invention refers to microelements, i.e. preferably microelectrodes or microphotodiodes, without being limited to this application. This also applies, in particular, to the exemplary embodiments mentioned below which discuss microelectrodes, although the statements in most cases are also applicable to microphotodiodes and similar microelements.

In addition, in the case of a microelectrode the result of a continuing attractive force is that the cells are pressed with a certain contact force against the microelectrodes, and the result thereof is a particularly good sealing resistance with respect to the reference electrode, and the adhesion is moreover also mechanically stable. The electrical resistance and thus the measurable signal (action potential) are substantially improved.

Although it is known from a different technical field (the so-called "patch-clamp technique") to aspirate cells by negative pressure against a pipette (cf. the U.S. periodical "Nature" Vol. 260, pp. 799–801, 1976), in the patch-clamp technique the pipette must be specifically guided to one individual cell. In the patch-clamp technique, the cells to which contact is to be made are not moved, since as a rule they are adhering to the substrate. The operation of making contact to cells using patch-clamp pipettes is substantially facilitated if the cells are immobilized by adhesion. Translocalization of adhering cells almost always results in lethal cell damage. The principal disadvantage of the patch-clamp technique lies in the limitation on the number of cells to which contact can be made simultaneously, since for space reasons it is impossible to introduce an arbitrarily large number of pipettes into the culture chamber. The invention, on the other hand, has the advantage that contact can be made simultaneously to a plurality of cells without the aforementioned space problems occurring.

The use of a base plate and of a cover plate separated therefrom offers advantages, in the context of the present invention, in particular when the arrangement according to the present invention is used repeatedly. For example, the base plate and the cover plate can be reused several times, either each individually or together. In addition, different manufacturing methods and materials can be used for the two plates.

Lastly, an advantage results, in terms of shaping of the electrode geometry, from the geometry (openings) of the cover plate and a resulting simplification in manufacture.

In a preferred embodiment of the arrangement according to the present invention, the means exert a negative-pressure force on the cells.

The advantage of this feature is that the necessary attractive force can be generated by purely mechanical means, i.e. by generating a negative pressure or vacuum.

In another exemplary embodiment of the invention, the means exert a hydrodynamic force on the cells.

The advantage of this feature is that the desired force can again be generated in simple fashion by generating a flow in the liquid biological environment.

It is further preferred if the means comprise channels which open out at a contact surface of the microelements.

The advantage of this feature is that the cells can be brought to the microelements and retained there, practical centering of the cells on the microelements being possible at the same time.

In this exemplary embodiment, it is further preferred if the channels can be connected to a source of negative pressure.

The cells can then, in the manner already mentioned, be brought against the contact surface by means of a negative-pressure force, and retained there.

In the alternative exemplary embodiment, the channels are connected to a pump device for the liquid environment. The pump device is preferably configured as an electroosmosis device.

The advantage of this feature is that the necessary hydrodynamic flow can be generated by simple electroosmosis. Given an identical channel cross section, it is possible with electroosmosis to generate a much greater hydrodynamic flow of the suspension as compared with standard negative-pressure devices. It is therefore possible in this fashion to attract cells with high efficiency from the more remote environment of the contact surface. The smaller the channel cross section, the greater the advantage of electroosmotic pumping over pneumatic pumps.

In a preferred development of this exemplary embodiment, the pump device, constituting an electroosmosis device, comprises two electrodes which are effective at opposite ends of the channels, a voltage being applied between the electrodes.

The advantage of this feature is that the desired electroosmotic device is implemented with extremely simple components.

It is further preferred if the means exert an electrostatic force on the cells.

This feature, too, has the advantage that simple technical means are used to exert the desired force on the cells in order to guide, isolate, or attract them.

In preferred exemplary embodiments of the invention which can also be used in isolation and in a different context, means are provided for guiding and/or isolating the cells prior to mechanical attraction onto the microelements.

The advantage of this feature is that individual cells can be brought in controlled fashion onto the microelements, so that defined conditions are created when contact is made to the cells.

The means preferably comprise funnel-like microcuvettes in the substrate, the microelements being located at the bottom of the microcuvettes.

The advantage of this feature is that the cells are captured by the funnel-like microcuvettes and are placed in controlled fashion onto the preferably annular electrodes. This happens regardless of whether the cells are attracted or whether they sink passively in response to gravity. The cells are thereby also mechanically centered on the microelectrodes.

It is preferred if surface regions between the microcuvettes are coated with a cell-repelling substrate.

The advantage of this feature is that passive sinking of the cells in response to gravity onto the spaces between the cuvettes can be prevented by coating the surface in the region of those spaces with a repulsive, i.e. cell-repelling substrate. The cells then sink preferentially into the funnels, i.e. the cuvettes, and then adhere on the bottoms of the cuvettes. This is the case in particular if the latter are coated with an attractive substrate.

According to the present invention, the substrate preferably comprises at least a base plate and a cover plate located thereabove.

The advantage of this feature is that the means for mechanically attracting the cells can be provided in defined fashion on the base plate and/or the cover plate as individual elements, for example as channel system, electrodes, microcuvettes, etc.

The base plate and/or the cover plate are preferably made of quartz, glass, silicon, or plastic, in particular of polystyrene, PMMA, or polyimide.

It is further preferred if the base plate and/or the cover plate are made of a material that is transparent to light, the wavelength of the light lying in a region of the spectrum accessible to microscopy techniques.

The advantage of this feature is that optical observation of the experiments is possible, using a microscope or the like.

In exemplary embodiments of the invention with plates layered one above another, it is preferred if the base plate equipped with the microelements is guided outward laterally as an edge connector.

The advantage of this feature is that easy electrical access to the microelements from outside is possible, and that the arrangement as a whole can easily be integrated into ordinary standardized electrical measurement setups.

It is moreover particularly preferred in this context if the base plate comprises at least a lower signal processing plate and an element plate located thereabove.

The advantage of this feature is that the very weak measurement signals sensed from the cells can immediately be processed over a short path length, so that a high signal-to-noise ratio can be attained.

In this case as well, it is analogously advantageous if the signal processing plate is guided outward laterally as an edge connector.

Good efficiency is furthermore obtained if the microelectrodes comprise sensing electrodes as well as stimulus electrodes and/or reference electrodes.

A multiple-electrode arrangement of this kind has the advantage that a wide variety of experiments can be performed under reproducible conditions.

Preferably the multiple electrodes are arranged concentrically with one another.

If a reference electrode is provided, it is preferably arranged at a distance above the sensing electrode, which is arranged at the bottom of the microcuvette.

In a preferred development of the arrangement according to the present invention, the surface of the microelectrode in contact with the environment is larger than the surface in contact with the cell.

The advantage of this feature is that the so-called Helmholtz capacitance is reduced. The reason is that the Helmholtz capacitance is governed by the surface area between electrode and electrolyte, i.e. the environment, but not by the surface area that is in contact with the cell.

In a preferred development of this exemplary embodiment, the microelectrode is configured as a chamber in a substrate, the chamber communicating through an opening with the external space surrounding the substrate.

The advantage of this feature is that in the configuration as a channel or a closed cavity, electrodes with a large surface area can be recessed in by plating the corresponding surface of the channel or cavity with, for example, gold. The sealing resistance with respect to the reference electrode is determined by the sealing of the cell-side channel or cavity opening, which can be kept small. Lower impedances, and thus better sensing properties, can be implemented with this arrangement. Instead of a cavity or a channel with a gold-plated surface it is also possible to use, for example, a sponge made of a noble metal, for example a platinum sponge. This arrangement is also usable outside the context of the present invention.

In exemplary embodiments of the method according to the present invention for making electrical contact, the force, as already mentioned, is preferably exerted as negative-pressure force or as hydrodynamic force, the latter preferably by means of electroosmosis, or as electrostatic force.

It is possible in this fashion to exert a contact force between cells and microelectrode, and/or a force for directed movement of the cells toward the microelectrodes.

In preferred variants of the method, the cells are stimulated via the microelectrodes, or potentials are sensed from the cells via the microelectrodes. Alternatively the luminescence of the cells and/or their light absorption can be measured via the microelements configured as microphotodiodes, as already explained above.

In the case of the method according to the present invention for manufacturing a microelectrode arrangement, preferably a channel system is configured in the base plate, microcuvettes are shaped in the cover plate, and the base plate is fitted to the cover plate in such a way that openings at the bottom of the microcuvettes are arranged in contact surfaces of the microelements and communicate with the channel system.

The advantage of these features is that the requisite elements for the means for mechanically attracting the cells in the microelement device can be manufactured using microstructure techniques that are known per se and controllable.

In a preferred exemplary embodiment of this method, the following steps are provided:
a) equipping the base plate and/or cover plate, on their surfaces facing one another, with a layer of molecules having a reactive terminal group;
b) fitting the base plate and cover plate together; and
c) activating a covalent bond between the layers by way of an external stimulus.

The advantage of this feature is that the base plate and cover plate can be assembled to one another in precise fashion, dispensing with mechanical joining elements and the like.

It is particularly preferred in this context if the base plate and cover plate are adjusted relative to one another after step b).

These features advantageously exploit the fact that prior to activation of the covalent bond, displacement of the base plate and cover plate relative to one another is still possible. The two parts can thus be aligned relative to one another in a mask aligner or a similar apparatus.

Only thereafter is the external stimulus applied, preferably as temperature, light, or an electric field.

In a further variant of the manufacturing method according to the present invention, the base plate and cover plate are joined to one another by anodic or metallic bonding.

Further advantages are evident from the description and from the appended drawings.

It is understood that the features mentioned above and those yet to be explained below can be used not only in the respective combinations indicated, but also in other combinations or in isolation, without leaving the context of the present invention.

SHORT DESCRIPTION OF THE DRAWINGS

Exemplary embodiments of the invention are shown in the appended drawings and will be explained in more detail in the description below. In the drawings:

FIG. 3 shows a further representation similar to FIGS. 1A and 1B, but for another exemplary embodiment of the invention;

DETAILED DESCRIPTION OF THE PREFERRED EMBODIMENTS

Figures 1A, 1B:
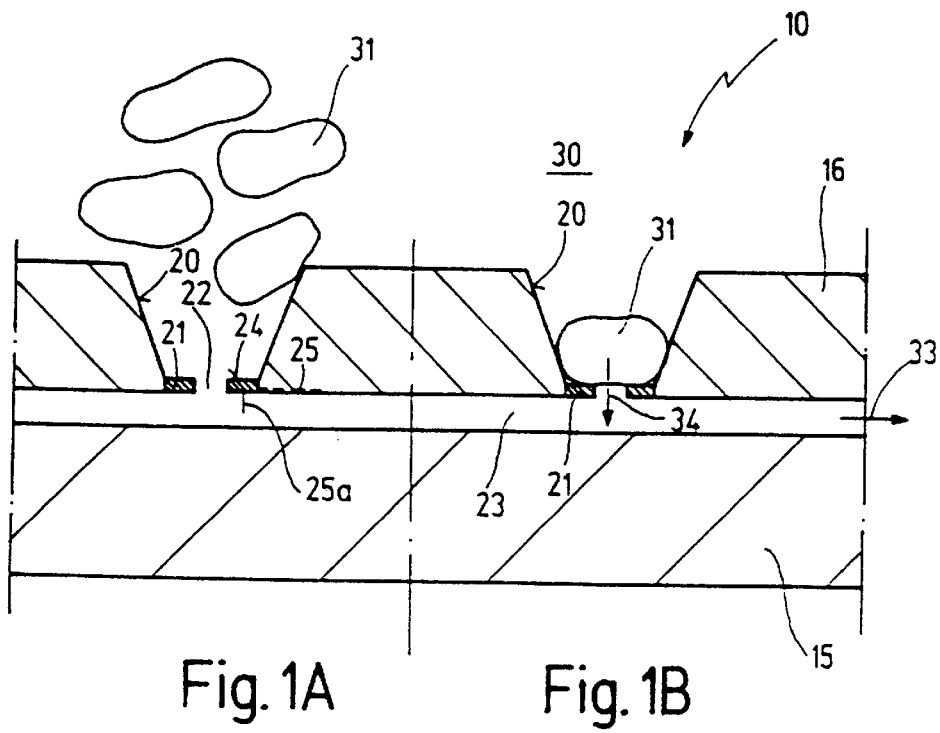
FIGS. 1A and 1B show an extremely schematic cross-sectional representation of an exemplary embodiment of a microelectrode arrangement according to the present invention, in two different operating phases.

In FIG. 1, 10 designates the entirety of a microelement device. The arrangement comprises substantially a two-layer substrate having a base plate 15 and a cover plate 16. As has already been mentioned, the microelectrodes discussed below are to be understood only as examples of microelements of various types. The invention is thus not limited to the application field of microelectrodes.

Funnel-like microcuvettes 20 are located in cover plate 16. Microcuvettes 20 taper at their undersides into annular electrodes 21. Annular electrodes 21 communicate via their central openings with a common channel 23, or can be guided outward individually.

Channel 23 is preferably shaped with microengineering methods in such a way that a trench is etched into the base plate. Channel 23 is then formed by setting the cover plate in place.

The upper sides of annular electrodes 21 serve as contact surfaces 24. Annular electrodes 21 can, for example, be connectable by way of conductive traces 25 in the separation plane between base plate 15 and cover plate 16, but other conductor paths are also possible, as indicated by 25a.

Located above arrangement 10 is a liquid biological environment or suspension or buffer solution, indicated as 30, in which biological cells 31 are present. Here again, the instance of a biological environment as electrolyte is to be understood as merely exemplary. It is also possible in the context of the present invention to use a suspension having artificial vesicles made of lipids, pores being incorporated into the vesicle shell as a model system for biological cells. The suspension then represents not a liquid biological environment but rather a liquid artificial environment.

As is evident from FIG. 1A, cells 31 are present in disordered fashion in environment 30.

When a negative pressure is then applied to common channel 23 as indicated by an arrow 33, cells 31 are aspirated onto annular electrodes 21.

It is apparent from FIG. 1B that a cell 31 rests on annular electrode 21 as a result of the effective negative pressure and is retained there, as indicated by an arrow 34.

The effect of microcuvettes 20 is that cells 31 are centered on annular electrodes 21 and on contact surfaces 24. The contact surface area between the cells and the microelectrodes is thus particularly large.

Figure 2:
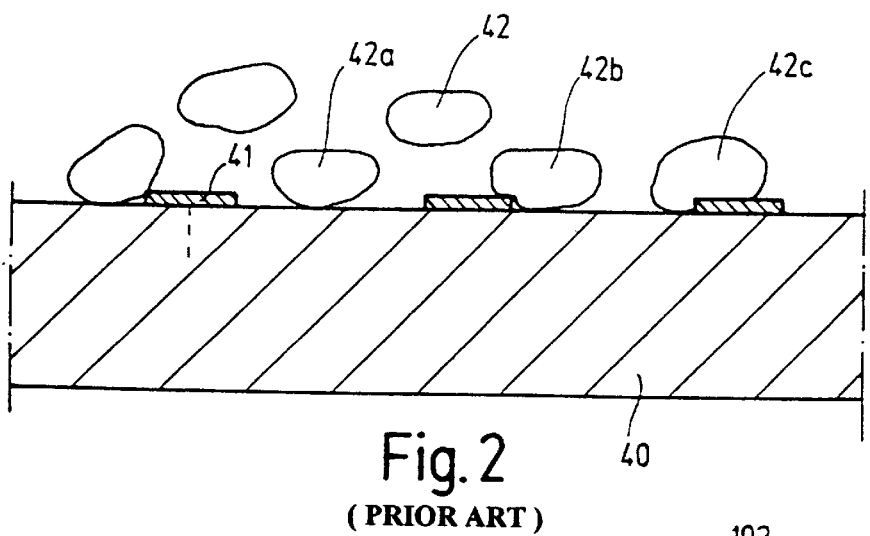
FIG. 2 shows a representation similar to FIGS. 1A and 1B, but for a microelectrode arrangement according to the existing art.

In contrast thereto, FIG. 2 shows a conventional arrangement. Isolated electrodes 41 sit on a substrate 40. Cells 42 then settle onto electrodes 41 in more or less random fashion. A cell 42a in FIG. 2, for example, sits only on substrate 40, and has absolutely no contact with an electrode 41. Cells 42b and 42c sit, for example, partially overlapping electrodes 41, the overlap ratio also being random.

FIG. 3 shows a further exemplary embodiment of the invention.

A microelectrode arrangement 50 once again comprises a base plate 51 and a cover plate 52. Microcuvettes 60, at the bottom of which annular electrodes 61 with contact surfaces 64 are located, are once again shaped in cover plate 52.

Base plate 51 comprises a channel system with stub channels 62 which open out centrally in annular electrodes 61. Stub channels 62 are in turn connected to a common channel 63. Here again (cf. FIG. 1), common channel 63 can be configured as a trench without stub channels.

To this extent, the exemplary embodiment according to FIG. 3 corresponds to the one according to FIGS. 1A and 1B.

In a departure therefrom, common channel 63 is connected to a reservoir 65. A first electrode 66 is located above cover plate 52. A second electrode 67 is located in reservoir 65. A voltage indicated by "+" and "−" is applied between electrodes 66, 67.

When the voltage is applied between electrodes 66 and 67, an electric field E is created tangentially to the walls of channel 63, as indicated by "E" in FIG. 3. This in turn results, in the electrolyte-filled channel 63, in electrolyte transport and thus in a hydrodynamic flow. The suspension present above cover plate 52, which is labeled 70 in FIG. 3, then flows toward microcuvettes 60. A force indicated with an arrow 72 is thereby exerted on cells 71 in suspension 70.

Cells 71 then settle in centered fashion onto annular electrodes 61, as has already been shown in FIG. 1B for the exemplary embodiment described therein.

Figure 4:
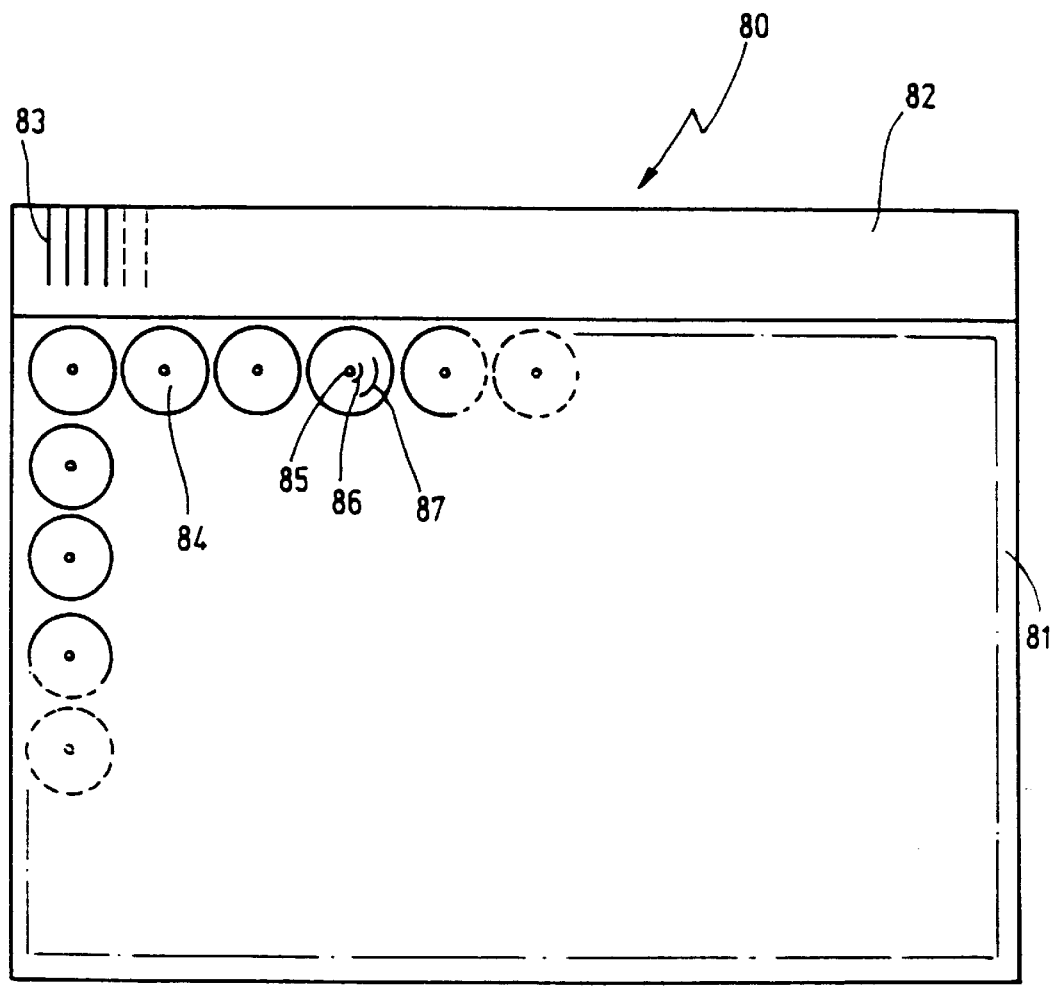
FIG. 4 shows a plan view of a further exemplary embodiment of a microelectrode arrangement according to the present invention.

FIG. 4 shows, in plan view, a further exemplary embodiment of a microelectrode arrangement 80. This comprises a plate arrangement 81 from which an edge connector 82 with contact tongues 83 projects laterally.

Cuvettes, for example 8×12=96 cuvettes, are recessed from above into plate arrangement 81; this number can also be substantially larger or smaller.

Indicated in one of the cuvettes 84 are a sensing electrode 85, a stimulus electrode 86, and a reference electrode 87. Electrodes 85, 86, 87 are preferably arranged concentrically with one another.

Figures 5, 6:
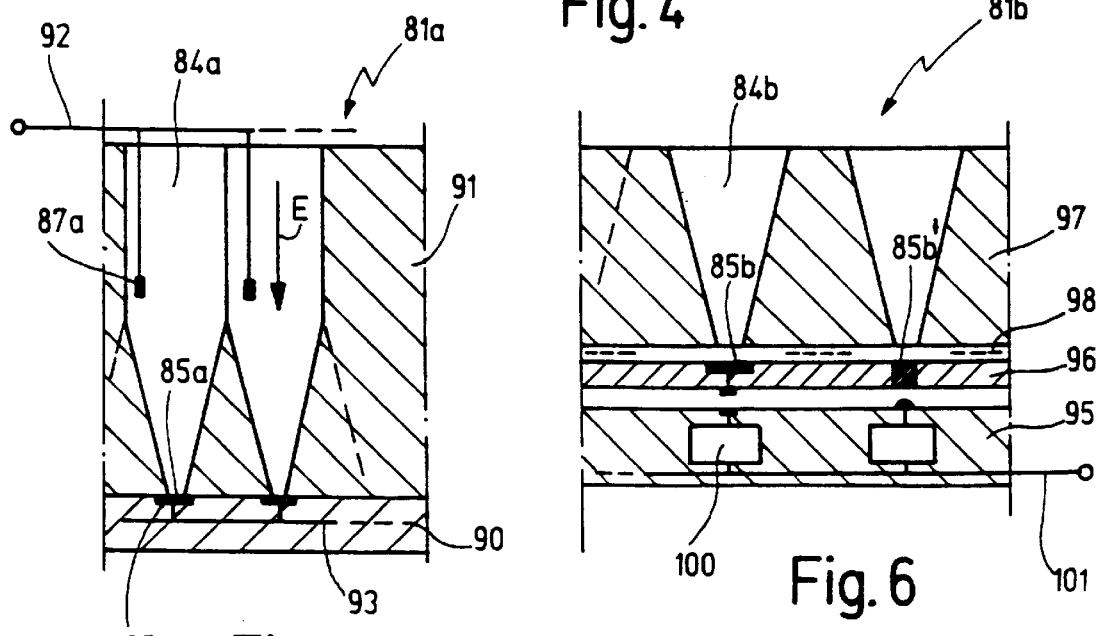
FIGS. 5 and 6 show, at enlarged scale, two representations of sections through microcuvettes that can be used in the arrangement according to FIG. 5.

Plate arrangement 80 is of multi-layer configuration, as has already been explained above. FIGS. 5 and 6 show, in section, two variants of the layered configuration.

In the variant according to FIG. 5, a base plate 90 and a cover plate 91 are provided. At least sensing electrodes 85 are located in base plate 90, while in cuvette 84a a reference electrode 87a is arranged at a distance above sensing electrode 85a.

Sensing electrodes 85a are connected to a line 93, and reference electrodes 87a to a line 92. It is understood that here and also in the other Figures, the line layout is to be understood as merely extremely schematic. The lines can be configured as single lines, multiple lines, or lines operated in multiplexed fashion.

FIG. 5 further indicates, with an arrow, an electric field E, which again can be used to exert an electrostatic force on cells, which are then guided downward along the oblique surfaces of cuvette 84a and ultimately sink onto sensing electrodes 85a. In general, however, the action of gravity will be sufficient.

In the variant according to FIG. 6, an at least three-layered arrangement is used. Located on a signal processing plate 95 is an electrode plate 96. Arranged above the latter, optionally by way of a seal 98, is a cover plate 97.

Amplifiers 100, optionally including impedance converters, filters, signal analyzers, or adapter components, are located in signal processing plate 95, amplifiers 100 being connected to the environment via lines 101.

At least sensing electrodes 85b, 85b'—which, as shown, can be configured in planar or rod-shaped fashion, or the like—are located in electrode plate 96.

Lastly, cover plate 97 contains cuvettes 84b that have already been mentioned several times. Reference electrodes can, of course, also be provided here at various places.

In the exemplary embodiments, electrode arrangement 10 or 50 or 80 respectively comprises, as mentioned, a base plate 15; 51; 90; 95, 96 and a cover plate 16; 52; 91; 97.

The plates can be equipped with suitable structures (conductive traces, electrodes, etc.), and can thereafter be bonded together. This can be accomplished either by conventional metallic bonding utilizing the conductive traces (cf. in FIG. 1A), or with the aid of thin organic layers.

In the latter case groups that are activated, for example, photochemically or thermally (examples in U.S. periodical "Int. J. Peptide Protein Res." Vol. 47, pp. 419–426, 1996), and which allow light-induced coupling of the two plates, are used. To manufacture arrangements 10; 50, the plates are each equipped, on their surfaces facing one another, with an ultrathin layer that is coupled covalently to the respective surface and is, for example, 10 nm thick and made up of molecules having reactive terminal groups. These layers allow a covalent join between the base plate and cover plate by way of an external stimulus, for example temperature, light, or an electric field. Prior to application of the stimulus, the plates can still be displaced relative to one another and thus aligned, for example in a mask aligner that is also used in photolithography. Other methods are also conceivable, however.

The plates can be shaped from a polymer using a punch technique. They can also be manufactured using ordinary microstructuring techniques.

Annular electrodes 21 and 61 provided on the bottom of microcuvettes 20 and 60, respectively, are preferably made of TiN, iridium, iridium oxide, platinum, platinum black, or gold. They can be chemically functionalized with a thin layer, so that preferably a specific interaction is induced with the cells that are to be adhered to.

It is particularly preferred if the microelectrodes are configured as ion-sensitive electrodes.

If the electrodes are equipped with a special surface coating, this results in specific fashion in an electrically sealing interaction with the cell membrane. Coatings that may be cited include, for example, lipid-like molecules, cell adhesion proteins or peptides, glycoproteins or glycopeptides, and hydrophobic coatings, although the aforesaid list is not limiting.

Figure 7:
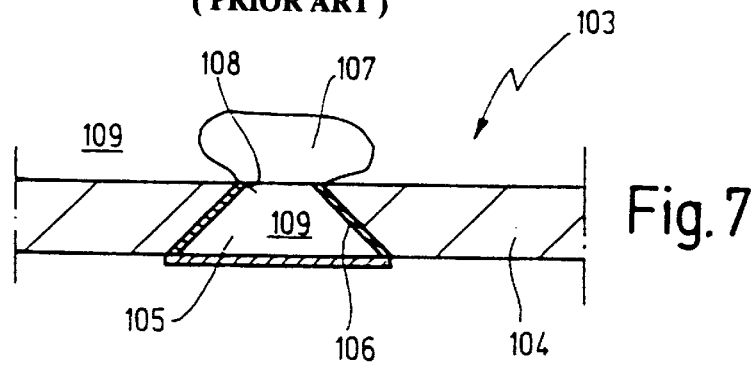
FIG. 7 shows, in a cross-sectional representation, a further embodiment of a microelectrode according to the present invention.

Lastly, FIG. 7 shows a further exemplary embodiment of a microelectrode arrangement 103 according to the present invention. A chamber 105 of, for example, truncated conical shape is located in a substrate 104. Chamber 105 is equipped on its walls with a conductive coating 106, in particular is goldplated. Chamber 105 can, as shown, be closed off at the bottom and equipped with a connector. Alternatively, however, it can also substitute for one of the channels that were mentioned earlier (for example, channel 62 in FIG. 3).

A cell 107 rests on the top of opening 108 of chamber 105. Since chamber 105 was open at the top before cell 107 came to rest, environment 109 used in arrangement 103, i.e. the respective electrolyte being used, has penetrated into chamber 105.

The result of this is that cell 107 rests on arrangement 103 only by way of a contact surface which corresponds to the annular surface of coating 106 in the region of opening 108. Electrode arrangement 103, on the other hand, is connected to electrolyte 109 over the entire surface of coating 106, so that this surface area is substantially greater.

It is understood in this context that the arrangement according to FIG. 7 is also to be understood only as an example. Instead of the arrangement shown therein, it is equally possible to use a sponge made of a noble metal, for example a platinum sponge.

EXAMPLE 1

Ninety-six microcuvettes with oblique walls were introduced into a plate. Electrodes were insert-molded into the bottom of the microcuvettes. The electrodes were made of gold wire, roughened by etching, with a diameter of 20 $\mu$m and a 10-$\mu$m projection. The projection on the underside was 200 $\mu$m. A signal processing plate beneath the cover plate equipped with the cuvettes was equipped with SMD impedance converters and amplifiers. Reference electrodes with an impedance of 1 k$\Omega$ were all contacted to one point. Nerve cells from embryonic chick brain were enzymatically dissociated and pipetted into the cuvettes. The cells sank onto the electrodes, where they formed aggregates with crosslinked cell structures. The signal amplitude was 200 $\mu$V.

EXAMPLE 2

A cover plate was equipped with 192 microcuvettes with conical walls. The bottom opening was 100 $\mu$m in diameter. The walls of the cuvettes were siliconized. Electrode plates with flat electrodes 1 mm in diameter were located at the bottom of the cuvettes. These electrodes were manufactured using thick-film technology on a ceramic plate. The surface of the electrodes was electroplated with platinum. By joining the cover plate to the electrode plate, the effective electrode surfaces were reduced to 100 $\mu$m, i.e. from 10 k$\Omega$ to 1 M$\Omega$. After the chick cells had been introduced, aggregates had formed, and the cells had sunk onto the electrodes (complete coverage), a sufficient signal-to-noise ratio was achieved up to a signal voltage of 4 mV.

EXAMPLE 3

Two hundred microcuvettes, with openings each 50 $\mu$m in diameter at the bottom, were formed in a cover plate. An electrode plate was equipped with conductive traces 10 $\mu$m wide at a spacing of 50 $\mu$m. The conductive traces were not insulated. They were manufactured by depositing gold by electroplating from a gold chloride solution until an electrode impedance of 100 k$\Omega$ was reached. The orientation of the conductive traces was perpendicular to the axes of the microcuvettes. The cover plate was clamped onto the electrode plate. A rubber spacer was provided for sealing. The result was three to four electrodes of 10×50 $\mu$m, which increased sensing reliability. The measurements were performed in each case differentially against a reference electrode introduced from above for each chamber. Neuroblastoma cells were carried over from cultures.

In addition, an electric field was applied in order to cause a migrating movement of the cells onto the electrodes.

EXAMPLE 4

The microcuvettes were equipped with a hole 0.5 mm in diameter. The oblique walls of the microcuvettes were siliconized. A rubber element was inserted between the plates for sealing. To form flat electrodes 2 mm in diameter, an electrode plate was electrically coated with gold black (10 k$\Omega$).

Altogether, arrangements with from two to several thousand cuvettes appear possible. The microcuvettes have a volume of between 1 $\mu$l and 100 $\mu$l. The electrode surface can have a diameter of between 1 $\mu$m and 1 mm.

The overall result of the invention is to make it possible to position individual cells or cell aggregates actively on specific cells of a multiple sensing electrode array and/or of a multiple-cuvette array. The invention has potential applications in the fields of pharmacology, pharmaceutical screening, neurobiology, and biosensors.

What is claimed is:

1. A microelement device comprising:
   a substrate having a plurality of cavities for receiving a liquid containing biological cells;
   a plurality of microelements each of which is arranged at a bottom of one of said cavities, each said microelement having a contact surface facing upwardly for electrically contacting one of said biological cells;
   a plurality of channels, each extending within said substrate and being in fluid communication with one of said microelements; and
   a negative pressure source in fluid communication with each said channel for attracting said cells toward said microelements.

2. The device as defined in claim 1, wherein said microelements are connected to amplifier means and wherein a reference electrode is provided for contacting a liquid received with said cavities.

3. The device as defined in claim 2, wherein the microelectrode comprises a surface being in contact with the environment and a surface being in contact with the cell, said surface being in contact with the environment being larger than the surface being in contact with the cell.

4. The device as defined in claim 1, wherein said microelements are connected to a voltage source, and wherein a reference electrode is provided for contacting a liquid received within said cavities.

5. The device as defined in claim 1, wherein said negative pressure source includes a pump means for said liquid.

6. The device as defined in claim 1, wherein said cavities are configured as funnel-like microcuvettes, said microelements being located at the bottom of said microcuvettes.

7. The device as defined in claim 6, further comprising surface regions between said microcuvettes, said regions being coated with a cell-repelling material.

8. The device as defined in claim 6, wherein said microcuvettes are coated with a cell-attracting layer of coating material.

9. The device as defined in claim 6, wherein said substrate comprises at least a base plate and a cover plate located thereabove.

10. The device as defined in claim 9, wherein the base plate is made of a material selected from the group consisting of glass, quartz, silicon, or plastic.

11. The device as defined in claim 9, wherein the cover plate is made of a material selected from the group consisting of glass, quartz, silicon, plastic, polystyrene, PMMA, and polyimide.

12. The device as defined in claim 9, wherein at least one element selected from the group consisting of the base plate and the cover plate is made of a material that is transparent to light, the wavelength of the light lying in a region of the spectrum accessible to microscopy techniques.

13. The device as defined in claim 9, wherein the base plate is connected to the microelements and comprises an edge connector which is guided outward laterally.

14. The device as defined in 9, wherein the base plate comprises at least a lower signal processing plate and an element plate located thereabove.

15. The device as defined in claim 14, wherein the signal processing plate is guided outward laterally as an edge connector.

16. The device as defined in claim 1, wherein the microelements comprise sensing electrodes and stimulus electrodes.

17. The device as defined in claim 16, wherein the microelements comprise reference electrodes.

18. The device as defined in claim 1, wherein the microelements comprise multiple concentrically arranged individual electrodes.

19. The device as defined in claim 6, wherein the microelements comprise at least one reference electrode and at least one sensing electrode, wherein said sensing electrode is arranged at the bottom of said microcuvette, and wherein said reference electrode is arranged at a distance above said sensing electrode.

20. A microelement device comprising
a substrate having a plurality of cavities for receiving a liquid containing biological cells;
a plurality of electrical microelements each of which is arranged at a bottom of one of said cavities, each said microelement having a contact surface facing upwardly for electrically contacting one of said biological cells and being electrically connected to a voltage source establishing an electric field directed for electrostatically attracting one of said cells toward said microelement, and a reference electrode for contacting liquid contained in said cavities.

21. The device as defined in claim 20, wherein said cavities are configured as funnel-like microcuvettes, said microelements being located at the bottom of said microcuvettes.

22. The device as defined in claim 21, further comprising surface regions between said microcuvettes, said regions being coated with a cell-repelling substrate.

23. The device as defined in claim 21, wherein said microcuvettes are coated with a cell-attracting substrate.

24. The device as defined in claim 21, wherein said substrate comprises at least a base plate and a cover plate located thereabove.

25. The device as defined in claim 21, wherein the microelements comprise at least one reference electrode and at least one sensing electrode, wherein said sensing electrode is arranged at the bottom of, said microcuvette, and wherein said reference electrode is arranged at a distance above said sensing electrode.

26. The device as defined in claim 20, wherein the microelements comprise sensing electrodes and stimulus electrodes.

27. The device as defined in claim 20, wherein the microelements comprise reference electrodes.

28. The device as defined in claim 20, wherein the microelements comprise multiple concentrically arranged individual electrodes.

29. A microelement device comprising a substrate comprising a plurality of cavities for receiving a liquid containing biological cells;

a plurality of electrical microelements each of which is arranged at a bottom of one of said cavities, each said microelement having a contact surface facing upwardly for electrically contacting one of said biological cells;

a plurality of channels, each extending within said substrate and being in fluid communication with one of said cavities; and an electroosmotic pump means cooperating with each said channel for attracting one of said cells toward one of said microelements.

30. The device as defined in claim 29, wherein said electroosmosis pump comprises two electrodes electrically coupled to opposite ends of said channels, a voltage being applied between the electrodes.

31. The device as defined in claim 29, wherein said cavities are configured as funnel-like microcuvettes, said microelements being located at the bottom of said microcuvettes.

32. The device as defined in claim 31, further comprising surface regions between said microcuvettes, said regions being coated with a cell-repelling substrate.

33. The device as defined in claim 31, wherein said microcuvettes are coated with a cell-attracting substrate.

34. The device as defined in claim 31, wherein said substrata comprises at least a base plate and a cover plate located thereabove.

35. The device as defined in claim 29, wherein the microelements comprise sensing electrodes and stimulus electrodes.

36. The device as defined in claim 29, wherein the microelements comprise reference electrodes.

37. The device as defined in claim 29, wherein the microelements comprise multiple concentrically arranged individual electrodes.

38. The device as defined in claim 31, wherein the microelements comprise at least one reference electrode and at least one sensing electrode, wherein said sensing electrode is arranged at the bottom of said microcuvette, and wherein said reference electrode is arranged at a distance above said sensing electrode.

* * * * *